United States Patent
Mayer Pujadas et al.

(10) Patent No.: US 10,765,523 B2
(45) Date of Patent: Sep. 8, 2020

(54) PROSTHESIS COMPONENT AND METHOD FOR THE PRODUCTION THEREOF

(71) Applicant: Zanini Auto Grup, S.A., Parets Del Valles (Barcelona) (ES)

(72) Inventors: Augusto Mayer Pujadas, Parets Del Valles (ES); Guillem Dominguez Santalo, Parets Del Valles (ES); Jose Sanahuja Clot, Parets Del Valles (ES); Francesc Xavier Gil Mur, Barcelona (ES); Miguel Punset Fuste, Barcelona (ES); Cristina Maria Caparros Vazquez, Barcelona (ES); Meritxell Molmeneu Trias, Barcelona (ES); Monica Ortiz Hernandez, Barcelona (ES)

(73) Assignee: Zanini Auto Grup, S.A., Parets Del Valles (ES)

( * ) Notice: Subject to any disclaimer, the term of this patent is extended or adjusted under 35 U.S.C. 154(b) by 15 days.

(21) Appl. No.: 15/749,918

(22) PCT Filed: Aug. 3, 2015

(86) PCT No.: PCT/ES2015/070603
§ 371 (c)(1),
(2) Date: Feb. 2, 2018

(87) PCT Pub. No.: WO2017/021563
PCT Pub. Date: Feb. 9, 2017

(65) Prior Publication Data
US 2018/0221158 A1 Aug. 9, 2018

(51) Int. Cl.
*A61F 2/34* (2006.01)
*A61F 2/36* (2006.01)
(Continued)

(52) U.S. Cl.
CPC .............. *A61F 2/3609* (2013.01); *A61F 2/30* (2013.01); *A61F 2/30965* (2013.01);
(Continued)

(58) Field of Classification Search
CPC .............. A61F 2/34; A61F 2310/00005; A61F 10/00407; A61F 2310/00023;
(Continued)

(56) References Cited

U.S. PATENT DOCUMENTS 6,596,225 B1    7/2003   Pope et al.
2007/0148462 A1*   6/2007   Hsiao .................. C23C 16/0272
                                                  428/408
(Continued)

FOREIGN PATENT DOCUMENTS

EP            0608997        8/1994
EP            1647242        4/2006
(Continued)

OTHER PUBLICATIONS

English Translation of FR2981277 reference (Year: 2013).*
International Search Report and Written Opinion issued in PCT/ES2015/070603, dated Mar. 28, 2016.

*Primary Examiner* — Brian A Dukert
*Assistant Examiner* — Rebecca Lynee Zimmerman
(74) *Attorney, Agent, or Firm* — BakerHostetler

(57) ABSTRACT

The prosthesis component (10), comprising a substrate (11) made of a polymeric material and a coating (12), characterized in that said coating (12) comprises titanium. The method for manufacturing the prosthesis component (10) comprising the stages of forming a polymeric substrate (11) and depositing a coating (12) on said polymeric substrate (11) comprising titanium by means of physical vapor deposition sputtering. It enables providing a prosthesis component that improves the fixation thereof, based on the forma- (Continued)

tion of a bioactive layer to improve the degree of osseointegration and, therefore, the fixation thereof to the bone.

16 Claims, 2 Drawing Sheets

(51) Int. Cl.
    *A61L 27/06*     (2006.01)
    *A61L 27/16*     (2006.01)
    *A61F 2/30*     (2006.01)
    *A61L 27/14*     (2006.01)
    *A61L 27/30*     (2006.01)

(52) U.S. Cl.
    CPC ............... *A61L 27/06* (2013.01); *A61L 27/14* (2013.01); *A61L 27/16* (2013.01); *A61L 27/306* (2013.01); *A61F 2/3094* (2013.01); *A61F 2/3662* (2013.01); *A61L 2420/08* (2013.01); *A61L 2430/24* (2013.01)

(58) Field of Classification Search
    CPC ...... A61F 2/3609; A61F 2/30; A61F 2/30965; A61F 2/3094; A61F 2/3662; A61F 2002/30004; A61F 10/00005; A61F 2420/08; A61L 2420/08; A61L 27/14; A61L 27/306; A61L 27/06; A61L 27/16; A61L 2430/24; B32B 15/04; C23C 16/0272; C23C 16/06; C23C 16/029; C23C 16/0281

See application file for complete search history.

(56) References Cited

U.S. PATENT DOCUMENTS

| | | | |
|---|---|---|---|
| 2007/0191962 A1* | 8/2007 | Jones | A61F 2/30767 |
| | | | 623/22.24 |
| 2011/0033661 A1* | 2/2011 | Oawa | A61F 2/30 |
| | | | 428/141 |
| 2011/0143127 A1* | 6/2011 | Gupta | A61L 27/30 |
| | | | 428/336 |

FOREIGN PATENT DOCUMENTS

| | | | | |
|---|---|---|---|---|
| EP | 2774631 | | 9/2014 | |
| ES | 2177570 | | 12/2002 | |
| FR | 2981277 A1 * | | 4/2013 | ............ A61L 27/04 |
| WO | WO2011058519 | | 5/2011 | |

\* cited by examiner

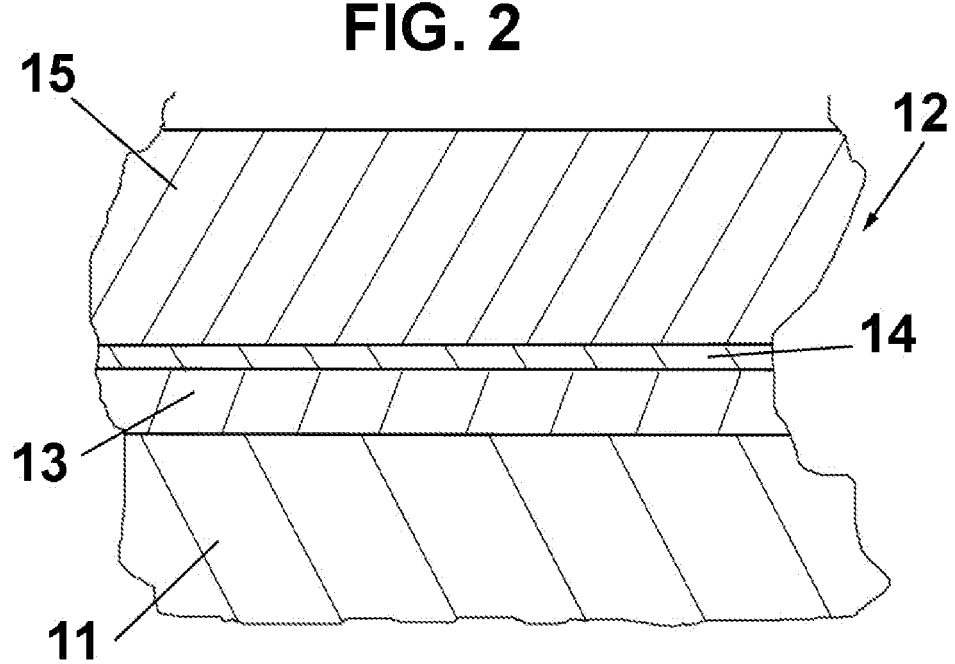

PROSTHESIS COMPONENT AND METHOD FOR THE PRODUCTION THEREOF

CROSS-REFERENCE TO RELATED APPLICATIONS

This application is a national-stage application under 35 U.S.C. § 371 (c) of International Application No. PCT/ES2015/070603, entitled "PROSTHESIS COMPONENT AND METHOD FOR THE PRODUCTION THEREOF," filed on Aug. 3, 2015, the entire disclosure and contents of which are hereby incorporated by reference.

DESCRIPTION

The present invention relates to a prosthesis component and to a manufacturing method thereof, which enables forming a bioactive layer in order to improve the degree of osseointegration, and therefore, fixation thereof to the bone.

BACKGROUND OF THE INVENTION

Prosthetic hip replacement is an operation designed to replace a hip joint that is damaged either due to trauma or some type of degenerative disease such as osteoarthritis. The hip is a joint made up of a bone sphere located at the proximal end of the femur, the femoral head, which is located within a cavity in the hip bone to which it adjusts perfectly. Hip prosthesis may comprise replacing the femoral head and/or the acetabulum. If the femoral head is replaced, the prosthesis further comprises a stem, which is inserted into the femur.

Currently, in most of the total systems of implanted hip prostheses, the stem is metallic (chromium-cobalt, stainless steel or titanium) mainly due to the high mechanical stresses that must be supported by said component once it has been implanted. The femoral head can be made of chromium-cobalt or some kind of ceramic material. As regards the acetabular component of the hip prosthesis, also known as acetabular cup and which is placed directly on the pelvis, the most widely used proposal today is composed of an ultra high molecular weight polyethylene body (UHMWPE) embedded inside a metal sheath, generally made of CoCr or titanium alloys with rough finishes in order to improve the anchoring thereof with the hip bone.

The use of UHMWPE in the acetabular cup requires the use of the metal sheath in order to fix this component to the bone, since the UHMWPE does not possess the osseointegrating capacity of other materials such as titanium after the application of certain preparation and/or treatment techniques. In spite of everything, sometimes this sheath can be loosened as a result of lack of bone fixation to the titanium cup. This is one of the main causes of failure in this type of component, which requires replacing the cup, provided that there is sufficient bone available for the replacement.

The clinical success of prostheses or implants used in bone tissue replacement is based on achieving osseointegration, i.e., the direct structural and functional connection between ordered, living bone and the surface of the implant. The improvement of short and long-term osseointegration is a function of multiple factors, among which the surface quality of the implant (physico-chemical and topographic) is of great importance. In fact, all the biological and mechanical interactions that occur between the implant and the surrounding tissues are through the interface created between said tissues and the surface of the implanted material.

Document U.S. Pat. No. 6,596,225 describes the use of diamond ceramic surface coatings deposited by means of PVD techniques, the main purpose of which is to increase the surface hardness of articulation surfaces in order to reduce the wear thereof. The ceramic nature of the diamond coating described in this document provides a bioinert nature to the coated surface, unlike the acetabular component of the present application, which provides a bioactive nature to the surface of the coating, which ensures the osseointegration thereof and the adherence thereof to the hip bone.

On the other hand, document EP0608997 describes the use of zirconium oxide ceramic surface coatings deposited by means of PVD techniques, the main purpose of which is to increase the surface hardness of articulation surfaces in order to reduce the wear thereof as well as improving corrosion resistance of the assembly by providing a barrier against the release of ions from these coatings.

Therefore, the purpose of the present invention is to provide a prosthesis component that improves the fixation thereof, based on the formation of a bioactive layer in order to improve the degree of osseointegration and, therefore, the fixation thereof to the bone.

DESCRIPTION OF THE INVENTION

The prosthesis component and the method of the invention solve the aforementioned drawbacks and have other advantages that will be described below.

According to a first aspect, the present invention relates to a prosthesis component that comprises a substrate of a polymeric material and a surface coating, and is characterized in that said coating comprises titanium.

It should be noted that the expression "prosthesis component" is intended to encompass any type of prosthesis component in orthopedic medicine, such as polymers for hard tissue replacement, polymeric components of articular prostheses (hip, knee, ankle, shoulder, wrist, elbow, among others) as well as implants intended for application in the lumbar spine, among the most outstanding.

According to a preferred embodiment, said coating also comprises chromium, and advantageously said coating comprises an anchoring layer in contact with the substrate and an outer surface layer comprising titanium.

Furthermore, said coating also preferably comprises a transition layer arranged between the anchoring layer and the outer surface layer, which may be made of a chromium-titanium alloy.

For example, said anchoring layer has a thickness comprised between 10 nm and 100 nm, said outer surface layer has a thickness comprised between 400 nm and 1000 nm, and said transition layer has a thickness comprised between 10 nm and 50 nm.

Advantageously, said coating has an outer roughness comprised between 3.5 and 4 μm, and said coating is deposited on the substrate by means of physical vapor deposition (PVD) sputtering.

Preferably, said polymeric substrate comprises ultra high molecular weight polyethylene (UHMWPE), highly cross-linked polyethylenes (HXLPE), high density polyethylene (HDP), polyether ether ketone (PEEK), polymethylmethacrylate (PMMA) and/or polyethylene (PE), or combinations thereof, and may also comprise vitamin E.

According to a second aspect, the present invention relates to a method for manufacturing a prosthesis component as described above, which comprises the stages of:

forming a polymeric substrate with a suitable design and a specifically textured surface finish in order to promote subsequent osseointegration on said surface; and depositing a coating on said polymeric substrate that comprises titanium by means of physical vapor deposition (PVD) sputtering.

The method according to the present invention also preferably comprises a surface bioactivation treatment stage subsequent to depositing said coating.

According to a preferred embodiment, said surface bioactivation thermochemical treatment stage comprises:

chemical treatment of the acetabular component to create a layer of sodium titanate gel on the outer surface of the coating;

dehydration of said sodium titanate gel layer by drying under controlled conditions; and heat treatment of the acetabular component.

For example, said chemical treatment comprises immersing the acetabular component in a NaOH solution at a temperature comprised between 40° C. and 140° C. for a period of time comprised between 6 hours and 72 hours, and said chemical treatment further comprises immersing the acetabular component in ultra pure water after immersing the acetabular component in the NaOH solution.

Furthermore, the drying can be carried out at a temperature comprised between 40° C. and 140° C. for a period of time comprised between 24 hours and 48 hours, and the heat treatment can be carried out for a period of time comprised between 60 and 180 minutes at a temperature comprised between 40° C. and 140° C.

Thus, a prosthesis component is provided that improves the fixation thereof, based on the formation of a bioactive layer in order to improve the degree of osseointegration and, therefore, the fixation thereof to the bone.

BRIEF DESCRIPTION OF THE DRAWINGS

For the purpose of helping to make the foregoing description more readily understandable, it is accompanied by a set of drawings, which, schematically and by way of illustration and not limitation, represent an embodiment.

FIG. 2 is a schematic sectional view of the detail of the layers that make up the coating of the acetabular component according to the present invention.

DESCRIPTION OF A PREFERRED EMBODIMENT

Figure 1:
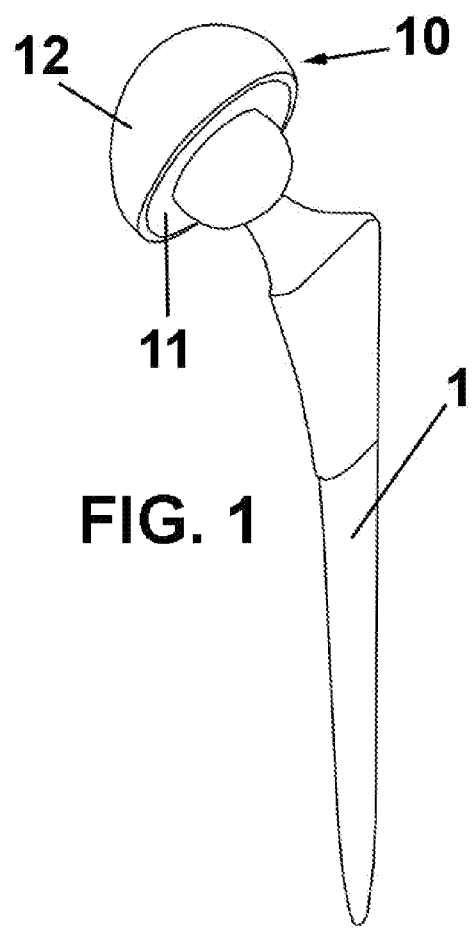
FIG. 1 is a perspective view of the hip prostheses comprising an acetabular component according to the present invention.

In the first place, it should be noted that the present description refers to a hip joint prosthesis for the sake of simplicity. However, the prosthesis component according to the present invention is applicable to any type of suitable prosthesis, as described above.

FIG. 1 shows a hip prosthesis comprising a stem 1 and an acetabular component, generally indicated by numerical reference 10.

FIG. 2 shows a cross-section of a polymeric substrate 11 and a coating 12 comprising an anchoring layer 13, a transition layer 14, and an outer surface layer, as described below.

It should be pointed out that for reasons of clarity the layers that make up the coating have only been represented schematically. In other words, this sectional view is not drawn to scale since, as will be described below, the differences in the thickness of the layers are big, and the layers do not have a smooth contact surface with each other, as represented in the drawing. In addition, the roughness of the coating has not been represented either so as not to hinder understanding of the drawing.

According to the manufacturing method of the present invention, first a coating 12 comprising titanium is carried out on the UHMWPE substrate 11 of the acetabular component 10, by means of physical vapor deposition sputtering (PVD-Sputtering) technology on the outer surface of the acetabular component, which is in contact with the pelvic cavity.

To this end, the specific technical characteristics of the acetabular component are defined:

Surface micro-roughness suitable for stimulating osteoblastic activity;

Press-fitted assembly of the cup in the acetabular cavity;

Thickness of the UHMWPE acetabulum that ensures fatigue resistance (cyclic load) of not less than 8 mm.

Furthermore, in order for the coating to be considered as an alternative to the current hip prosthesis acetabulae, it must have the following properties:

Good adhesion between the coating and the polymeric substrate;

A bioactive surface that stimulates osseointegration;

Roughness suitable for stimulating osteoblastic activity.

To this end, the acetabulum according to the present invention is made of a single piece (monobloc) to eliminate problems of adhesion and wear between layers, as well as to minimize the action of possible bone absorption phenomena due to stress shielding.

According to a preferred embodiment, the coating comprises an outer layer of titanium and a gradation of metallic layers of other materials, in order to favor adhesion of the metallic layer on the substrate (UHMWPE). Other possible biocompatible materials for the outer layer could consist of pure titanium or titanium alloys such as Ti6Al4V, Tantalum and the alloys thereof, Cr—Co alloys, zirconia and niobium. These layers are deposited by means of PVD.

The technical characteristics of the metallic layers are detailed below:

Anchoring Layer 13:

The purpose of this coating area is to ensure good adhesion and strong anchoring between the lower area of the coating of a metallic nature and the surface of the component substrate of polymeric nature. This first layer of the coating consists of a thickness comprised between 10 nm and 100 nm and a uniform composition of metallic chromium (Cr).

The thickness of this first layer of coating ensures excellent anchoring between the UHMWPE polymeric substrate and the rest of the coating, maintaining at all times the level of roughness and surface topography generated during injecting forming of the substrate of the UHMWPE acetabular component.

The coating of an intermediate layer between the titanium and the substrate will serve to increase adhesion by creating a bond between layers that is not only mechanical but also physical and chemical.

Intermediate Transition Layer 14:

The transition area of the coating is located immediately after the first anchoring layer of the coating, which is in direct contact with the surface of the UHMWPE polymeric substrate. The transition layer is placed between the anchoring layer in direct contact with the surface of the substrate and the surface layer of the coating in direct contact with the bone tissue of the hip.

The purpose of this transition layer is to ensure a gradual and uniform transition between the mechanical properties existing between the anchoring layer and the surface layer. This transition layer has an approximate thickness comprised between 10 nm and 50 nm of variable composition, made up of a mixture of chromium and titanium. The composition of the transition layer will vary gradually from a 100% chromium-based composition up to a final composition of 100% Titanium.

The use of PVD technology enables the formation of gradual composition coatings, the main advantages of which are the following:
  Gradual transition of mechanical properties along the thickness of the layer avoiding any problems related to the generation of internal stresses in the coating;
  No borders between layers inside the coating, which greatly increases the structural stability of the coating and fatigue resistance thereof;
  The possibility of taking advantage of the synergistic effect of different coating compositions within a single-layer structure, which allows the presence of a composition in the anchoring layer that ensures optimum adhesion and fixation of the coating, in addition to an optimal surface layer from the biological and osseointegrating point of view.

Just like in the anchoring layer of the coating, the thickness of the transition layer of the coating also maintains the level of roughness and surface topography generated during injection forming of the UHMWPE substrate of the acetabular component.

Outer Surface Layer 15:

The outer surface layer of the coating is located immediately on top of the intermediate transition layer. The surface layer is located between the transition layer and the bone tissue surface of the hip.

The composition of this surface layer is based on pure titanium (Ti gp2), which, as it is in direct contact with the bone tissue of the hip, ensures the biocompatible nature of the coating and prevents the harmful formation of fibrous tissue on the surface thereof, as a possible response of the body to the presence of foreign matter.

The presence of a surface layer consisting solely of pure titanium (Ti gp2) offers a great number of advantages, the most important of which are summarized below:
  It ensures the biocompatibility of the coating, thus avoiding fibrotic encapsulation of the surface thereof, which would cause the prosthetic system to fail;
  It makes it possible to carry out subsequent thermochemical treatment, which will ensure the bioactivity of the coating surface, described below, but which will ensure the osseointegration of the coating;
  It provides great resistance to corrosion of the coating together with the effect of a barrier against the release of ions produced by the titanium layer.

The purpose of this surface layer of the coating is ensuring the biocompatibility of the coating and making it possible to carry out the subsequent thermochemical bioactivation treatment. This third and last layer of coating has an approximate thickness comprised between 400 nm and 1000 nm of titanium alloy, for example, metal titanium (Ti gp2).

Just like in the anchoring layer of the coating, the thickness of the transition layer also maintains the level of roughness and surface topography generated during injection forming of the UHMWPE substrate of the acetabular component.

Topography is a critical factor for osseointegration. Improved osseointegration properties accelerate the patient's recovery process, since they result in faster and more effective osseointegration. According to research carried out by the inventors of the present application, the most appropriate level of roughness for fixing osteoblasts on the surface of the coating would be comprised between 2 and 6 µm (Ra).

The external topography of the implant, once the metallic coating has been applied, must copy the initial roughness existing on the surface of the polymeric component, or have a controlled roughness favorable to osseointegration. Furthermore, it must have sufficient thickness to enable carrying out a subsequent thermochemical bioactivation treatment without completely damaging the coating.

Using the PVD process achieves that the metallic coating obtained reproduces the average roughness that exists on the surface of the polymeric substrate.

Once the surface coating of the substrate of the acetabular component has been performed, a surface bioactivation treatment is carried out in order to provide the coating with osteoinductive characteristics, which stimulate and accelerate the creation of natural bone on said surface. As a result, the bioactivated surface layer in contact with the physiological fluids will cause a layer of in vivo apatite to be deposited on the treated surface.

The bioactivity treatment consists of a thermochemical treatment. Said treatment comprises three main stages:

The first stage consists of a chemical treatment of the surface in order to create a sodium titanate hydrogel on the titanium coating, which is obtained by immersing the component in a NaOH solution at a temperature comprised between 40° C. and 140° C. for a period of time comprised between 6 hours and 72 hours.

The second stage consists of drying at a temperature comprised between 40° C. and 140° C., for a period of time comprised between 6 hours and 72 hours.

The third stage consists of carrying out a heat treatment for an approximate period of time comprised between 60 and 300 minutes at a temperature comprised between 40° C. and 140° C., which provides stability to the hydrogel that has been formed.

The purpose of this drying process is to dehydrate said layer in the form of sodium titanate hydrogel in order to dehydrate, densify and increase the adhesion to the substrate of said layer. As a result of carrying out the heat treatment, a stable and partially crystalline $Na_2TiO_3$ layer is obtained, which promotes bioactivity and improves the surface properties thereof.

Once said bioactivation treatment was carried out, it was verified that both the titanium outer layer and the anchoring layer support the chemical treatment without perforating the coating during the chemical treatment, or affecting adhesion/joining between the different layers that make up the coating.

The homogeneity and thickness of the coating were evaluated by means of scanning electron microscope (SEM) and focused ion beam (FIB). The adhesion of the coating with respect to the substrate was evaluated by means of a Scratch test.

Carrying out the bioactivation treatment on the coated components must meet a number of critical requirements, which are described below:
  Ensuring the structural stability and bioactivity of the system;
  Ensuring that no surface contaminant of any kind is introduced, which could be harmful under in vivo conditions once implanted;

Maintaining unaltered the surface roughness levels of the samples treated before carrying out the treatment, in order to ensure the most appropriate level of roughness for fixing the bone on the surface of the coating.

On the other hand, as UHMWPE implants are not stable at 600° C., the heat treatment was optimized, using a temperature range in which the sodium titanate hydrogel was stabilized without damaging the polymeric substrate or separating the metallic layer.

The homogeneity and thickness of the coating were evaluated by means of scanning electron microscope (SEM) and focused ion beam (FIB).

Prediction of the bioactive nature of the treated coating was accomplished by immersing the samples in simulated body fluid (SBF), as indicated in the specifications of ISO Standard 23317. The samples treated by using the optimal conditions resulting from this study show compounds with an apatitic composition after immersion thereof in SBF. The homogeneity and surface chemical composition of the metallic coating was evaluated by means of scanning electron microscope (SEM) and energy disperse spectroscopy (EDS).

FIB microscope analysis of the cross-section of the coating made it possible to observe the effect of the bioactivation treatment on the structural integrity of the layer/substrate assembly. SEM micrographs make it possible to observe the penetration depth of the bioactive treatment, which translates into the final thickness of the sodium titanate layer formed on the titanium surface layer, which was comprised between 300 and 800 nm. Carrying out this stage of the study made it possible to determine the optimum minimum thickness for ensuring the structural integrity of the coating, which was set at an approximate value of 500 nm.

As an example of the developed coating, the PVD deposition of the coating was carried out with a 50 nm thick anchoring layer, followed by a 50 nm thick Cr—Ti composition gradient layer, to finally create an 800 nm thick titanium surface layer. Carrying out the bioactivation treatment consisted in a first stage of alkaline attack by immersion in a solution of 2.5M NaOH at 80° C. for a period of 48 hours, after which it was rinsed with water followed by drying at 100° C. for 12 hours. After drying, a heat treatment was carried out at 120° C. for 300 minutes. The depth of the alkaline attack reached a thickness of 500 nm, ensuring the structural stability of the layer-substrate system.

The biocompatibility of the samples was evaluated by carrying out in-vitro cytotoxicity tests, following the specifications established by international UNE-EN ISO Standard 10993 (Biological evaluation of medical devices), using indirect exposure as a method for evaluating cytotoxicity.

The analysis of the results showed no relevant cytotoxic effects of the samples analyzed by indirect exposure on the SAOS-2 cells, which ensures good behavior of the material inside the human body once implanted while also ensuring biocompatibility thereof.

The level of cell proliferation experienced on the samples was analyzed at different time periods, measuring the proliferation 7 days, 14 days and 21 days after cell culture. The analysis of the results made it possible to observe an increase in proliferation among the days that were studied, showing the highest values of proliferation between 14 and 21 days after cell culture.

The analysis of the results made it possible to observe a clear progressive increase in the expression of Alkaline Phosphatase (ALP) gene activity from 7 days to 21 days, which would be a clear indication of the cell differentiation process. The activity and the expression of the Alkaline Phosphatase gene are directly related with the mineralization of the bone matrix, which is used as a differentiation marker of the osteoblastic phenotype and an indicator of bone formation and replacement. The evidence collected and published at the scientific level up to date enables establishing a direct relationship between the presence of ALP and the normal development of bone tissue in the human body.

Ultimately, the results obtained not only show a clear increase in cell proliferation in contact with the surface of the samples but also make it possible to observe a cell differentiation (specialization) towards the formation of bone cells, which are the most relevant type of cells for ensuring good anchoring and good transmission of stress between the prosthesis and the surrounding bone thereof.

Despite the fact that reference has been made to a specific embodiment of the invention, it is evident for the person skilled in the art that numerous variations and changes can be made to the described acetabular component and the manufacturing method thereof, and that all the aforementioned details may be substituted by other technically equivalent ones, without detracting from the scope of protection defined by the attached claims.

The invention claimed is:

1. A prosthesis component comprising a substrate made of a polymeric material and a coating, wherein said coating comprises an anchoring layer in contact with the substrate, an outer surface layer comprising titanium, and a transition layer arranged between the anchoring layer and the outer surface layer, said transition layer being made of chromium and titanium mixture.

2. The prosthesis component according to claim 1, wherein said anchoring layer of the coating is made of chromium.

3. The prosthesis component according to claim 1, wherein said anchoring layer has a thickness of between 10 nm and 100 nm.

4. The prosthesis component according to claim 1, wherein said outer surface layer has a thickness of between 400 nm and 1000 nm.

5. The prosthesis component according to claim 1, wherein said transition layer has a thickness of between 10 nm and 50 nm.

6. The prosthesis component according to claim 1, wherein said coating has an outer roughness of between 2 and 6 μm.

7. The prosthesis component according to claim 1, wherein said coating is deposited on the substrate by means of physical vapor deposition (PVD) sputtering.

8. The prosthesis component according to claim 1, wherein said polymeric substrate comprises ultra high molecular weight polyethylene (UHMWPE), highly cross-linked polyethylenes (HXLPE), high density polyethylene (HDP), polyether ether ketone (PEEK), polymethylmethacrylate (PMMA), polyethylene (PE), or combinations thereof.

9. The prosthesis component according to claim 1, wherein said polymeric substrate further comprises vitamin E.

10. A method for manufacturing said prosthesis component according to claim 1, comprising the stages of:
    forming said polymeric substrate; and
    depositing said coating on said polymeric substrate by means of physical vapor deposition (PVD) sputtering, and
    forming a transition layer arranged between an anchoring layer and an outer surface layer of the prosthesis component, said transition layer being made of a chromium and titanium mixture.

11. The method for manufacturing a prosthesis component according to claim 10, further comprising a surface bioactivation treatment stage subsequent to forming and polymeric substrate.

12. The method for manufacturing a prosthesis component according to claim 11, wherein said surface bioactivation treatment stage comprises:
chemical treatment of the component to create a layer of sodium titanate gel on the coating;
drying of said sodium titanate gel layer; and
heat treatment of the component.

13. The method for manufacturing a prosthesis component according to claim 12, wherein said chemical treatment comprises immersing the component in a NaOH solution at a temperature of between 40° C. and 140° C. for a period of time of between 6 hours and 72 hours.

14. The method for manufacturing a prosthesis component according to claim 13, wherein said chemical treatment further comprises immersing the component in ultra pure water after immersing the component in the NaOH solution.

15. The method for manufacturing a prosthesis component according to claim 12, wherein said drying is carried out at a temperature of between 40° C. and 140° C. for a period of time of between 6 hours and 72 hours.

16. The method for manufacturing a prosthesis component according to claim 12, wherein said chemical treatment is carried out for a period of time of between 60 and 300 minutes at a temperature of between 40° C. and 140° C.

* * * * *